United States Patent
Rauls et al.

(10) Patent No.: US 6,534,680 B1
(45) Date of Patent: Mar. 18, 2003

(54) DICARBOXYLIC ACID CRYSTALLIZATES

(75) Inventors: Matthias Rauls, Limburgerhof (DE);
Dieter Baumann, Frankenthal (DE);
Hermann Wistuba, Mannheim (DE);
Bernhard Otto, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/367,233

(22) PCT Filed: Feb. 9, 1998

(86) PCT No.: PCT/EP98/00703
§ 371 (c)(1),
(2), (4) Date: Oct. 27, 1999

(87) PCT Pub. No.: WO98/35929
PCT Pub. Date: Aug. 20, 1998

(30) Foreign Application Priority Data

Feb. 12, 1997 (DE) .......................... 197 05 329

(51) Int. Cl.[7] .................. C07C 55/00; C07C 55/06; C07D 333/22
(52) U.S. Cl. .................. 562/590; 562/593; 562/597; 549/72
(58) Field of Search ................ 562/580, 582, 562/597, 593, 590; 549/72

(56) References Cited

U.S. PATENT DOCUMENTS

| | | | |
|---|---|---|---|
| 3,102,908 A | * 9/1963 | Raynes | 562/580 |
| 3,330,665 A | 7/1967 | Van Ness | 99/78 |
| 3,459,798 A | 8/1969 | Lassiter et al. | 260/537 |
| 3,770,390 A | * 11/1973 | Teot | 23/300 |
| 3,815,252 A | 6/1974 | Skuce et al. | 34/8 |
| 3,883,640 A | * 5/1975 | Smart | 423/415.1 |
| 4,254,283 A | * 3/1981 | Mock | 562/530 |
| 4,874,700 A | * 10/1989 | Seipenbusch | 204/542 |
| 5,034,105 A | * 7/1991 | Berglund et al. | 204/538 |
| 5,104,492 A | * 4/1992 | King et al. | 203/15 |
| 5,296,639 A | * 3/1994 | Klug et al. | 562/593 |

FOREIGN PATENT DOCUMENTS

| DE | 1618796 | 6/1967 |
|---|---|---|
| DE | 2303627 | 1/1973 |

OTHER PUBLICATIONS

Database WPI, Section Ch, Week 8541, Derwent Publications Ltd., AN 85–253810 (JP 60 169 436).

Davey et al., *J. Chem. Soc. Faraday Trans.*, 1992, 88(23), 3461–3466.

* cited by examiner

*Primary Examiner*—Ceila Chang
*Assistant Examiner*—Taylor V Oh
(74) *Attorney, Agent, or Firm*—Keil & Weinkauf

(57) ABSTRACT

Dicarboxylic acid crystals are prepared from a solution containing at least one organic dicarboxylic acid in a process in which at least one anionic polyelectrolyte having a molecular weight of at least 2000 is added to the solution before or during the crystallization.

8 Claims, No Drawings

DICARBOXYLIC ACID CRYSTALLIZATES

The present invention relates to a process for preparing dicarboxylic acid crystals, in particular free-flowing and storable dicarboxylic acid crystals, and to free-flowing and storable dicarboxylic acid crystals. The invention furthermore relates to the use of one or more anionic polyelectrolytes in the preparation of dicarboxy-lic acid crystals.

Crystalline dicarboxylic acids, and among these especially adipic acid, are widely used in chemical synthesis, for example for preparing polymers, especially polyamides. To ensure ease of processing and manipulation, the dicarboxylic acids are usually converted into crystal powders (crystals). However, the average size distribution of these crystals should not be too small in order, for example, to reduce or avoid dust formation during handling.

However, on lengthy storage of such crystals in heaps they display the property of caking together to form larger crystallites. Larger transport and storage containers such as big bags or silos can therefore often be emptied only with expenditure of considerable mechanical force to break up caked crystals. This circumstance causes, for example when adipic acid is used, an unwanted additional expenditure of time and money.

Adipic acid crystallizes from pure solutions usually in the form of thin leaflets which have a large contact area and thus, because of the attractive interactions between the individual contact areas, make good adhesion between adjacent crystals possible. Adipic acid crystals are described, for example, in R. J. Davey et al. in J. Chem. Soc. Faraday Trans., 88(23), (1992) 3461-3466.

It is also explained in the abovementioned literature that the surface of pure adipic acid crystals is essentially determined by the crystallographic planes which are oriented in the {100} direction and whose physical properties derive from the hydrophilic carboxyl groups located there. If two such {100} planes come into contact, they are able immediately to adhere weakly to one another through formation of hydrogen bonds. In the presence of minute amounts of water, it is then possible on lengthy storage for a more stable crystalline bridge to be constructed between the crystals. The formation of such crystalline bridges is responsible for the caking of the crystals described above.

Another disadvantage of adipic acid crystals is attributable to the fact that the crystal plates formed are very thin. Thin crystal plates are very easily broken during preparation or processing and thus produce a fines content which is usually unwanted. On the one hand, the widening of the crystal size distribution associated with this is often empirically thought to be connected with a deterioration in the flow behavior and, on the other hand, the fines content results in dust formation during processing, which may cause losses of product and, where appropriate, elaborate procedures have to be carried out to ensure safe working.

A number of physical and chemical processes allowing the caking process to be suppressed are described in the prior art. Thus, for example, when adipic acid is stored in a product silo, small amounts of a dry gas are continuously passed through the silo. Since this gas stream substantially removes traces of moisture which are always present, there is essentially no formation of intercrystalline bridges, and caking can thus be substantially prevented. This method has, however, the disadvantage that it can be applied to transport containers only with difficulty, and in particular not to big bags.

Another method for suppressing strong intercrystalline adhesion is to cover the crystals with hydrophobic agents. Thus, for example, DE-A 1,618,796 describes several possible ways of rendering the surface of adipic acid crystals hydrophobic by applying monocarboxylic acids thereto, and thus preventing the formation of intercrystalline bridges. The disadvantage of this process is that from 20 to 100 ppm of fatty acids must be added to the adipic acid, and these remain in the product and thus make it unsuitable for applications with high purity demands. In addition, this method requires an additional process step in the preparation of the adipic acid. U.S. Pat. No. 5,296,639 describes a process for purifying adipic acids during crystallization, in which the crystal morphology is modified so that uptake of impurities during the crystallization is reduced. For this purpose there is addition, for example, of caproic acid or selected surfactants such as sodium dodecyl sulfate, sodium dodecylsulfonate or sodium dodecylbenzenesulfonate. A disadvantage of this process is that the additives typically have to be added in concentrations of more than 100 ppm and up to 3% in order to achieve the desired effect. This usually results in unacceptable contamination of the product. An additional disadvantage on use of surfactants is that, if there is a rise in level due to internal recycling of the solvent (usually water) in systems, they lead to foaming so that use in the specific industrial process is usually made difficult or even becomes absolutely impossible.

The DE-OS2,303,626 relates to the crystallization of peroxy salts, where one or more water-soluble polyelectrolytes are added to the peroxy salt containing solution before crystallization. The document mentions the addition of polyacrylates, it does, however, not mention the importance of the molecular weight. Furthermore, it can not be taken from the document that already a small amount of polyelectrolyte is sufficient to obtain dicarboxylic acid crystals with sufficient size and stability along with a low residual humidity content and excellent freeflow ability, based on a special isometry of the crystals.

It is an object of the present invention to provide a process for preparing dicarboxylic acid crystals which do not have the abovementioned prior art disadvantages. It was a particular object of the invention to provide, by means of a suitable process, dicarboxylic acid crystals which show good flow behaviour and do not lose their flowability even on lengthy storage either in product silos or in transport containers such as big bags. It was likewise an object of the invention to provide dicarboxylic acid crystals which show no great tendency to form fines either during preparation or during handling, transport or before or during processing. It was another object of the invention to provide, by means of a suitable process, dicarboxylic acid crystals which have high product purity and-are substantially free of contamination by coating agents or crystallization aids.

We have found that these objects are achieved by subjecting a solution of a dicarboxylic acid to crystallization with addition of at least one anionic polyelectrolyte having a molecular weight of at least 2000 as crystallization aid.

The invention thus relates to a process for preparing dicarboxylic acid crystals from a solution containing at least one organic dicarboxylic acid, adding to the solution, before or during the crystallization, at least one anionic polyelectrolyte having a molecular weight of at least 2000.

All numerical data in the present text relate to the weight of the components identified in each case, unless expressly indicated otherwise. The term "polyelectrolyte" which is used for simplicity in the present text always relates to the whole crystallization aid used, ie. both to a single polyelectrolyte and to a mixture of at least two polyelectrolytes.

The dicarboxylic acid crystals obtainable by this process are distinguished by good flowability, long storability without caking, low residual moisture before the drying step, and an average crystal size which is distinctly increased by comparison with conventional crystals.

Another advantage of the invention is that when a high molecular weight anionic polyelectrolyte as defined for the purpose of the present invention is used, in contrast with the use of low molecular weight compounds as crystallization aids, even extremely low concentrations, for example a few ppm based on the complete crystallization solution, suffice to achieve the desired effect of free-flowing and storable crystals with an average crystal size which is increased by comparison with conventional methods, and with a narrow crystal size distribution, and thus a low fines content.

When such small amounts of crystallization aid as are envisaged for the purpose of the invention are added, in contrast to conventional monomeric additives, the amount of crystallization aid remaining in the crystals is no more than only just measurable and causes insignificant contamination having an adverse effect on further processability of the adipic acid. As a rule, the content of crystallization aid in the crystals on application of the process according to the invention is below about 20 ppm, preferably below about 10 ppm and particularly preferably below about 5 ppm.

The low concentrations additionally make it possible to avoid interference, such as foam formation caused by surfactants, during process steps connected with the adipic acid crystallization and, where appropriate, later processing steps. Addition of the crystallization aid produces an increase in the average crystal size of up to 50% and a crystal lattice which, on visual assessment, has fewer faults. These effects result in greater hardness and less sensitivity to abrasion (reduction in the fines content in subsequent process steps) of the crystals. Furthermore, removability of water from the fresh crystals is improved, and thus the residual moisture content of the crystals before the drying step is lower (facilitated drying).

All organic dicarboxylic acids are suitable as dicarboxylic acid for use in the process according to the invention. These are, in particular, oxalic acid, malonic acid, succinic acid, glutaric acid, adipic acid, pimelic acid, maleic acid, fumaric acid and other higher, saturated or unsaturated, branched or unbranched dicarboxylic acids. The dicarboxylic acids may also contain other functional groups such as hydroxyl groups or substituents such as halogen atoms.

The use of adipic acid represents a preferred embodiment in the implementation of the process according to the invention.

In the process according to the invention for preparing dicarboxylic acid crystals, at least one anionic polyelectrolyte having a molecular weight of at least about 2000 is added to a solution containing at least the dicarboxylic acid to be crystallized. The polyelectrolyte advantageously has a molecular weight of about 20,000 to about 2,000,000 and a molecular weight of about 100,000 to 500,000 is preferred for the purpose of the invention. In an advantageous embodiment of the invention, a polyelectrolyte having a molecular weight of about 200,000 to about 300,000 is employed.

Suitable as anionic polyelectrolyte is in principle any macromolecule which has a sufficient number of anionic groups in the molecule to achieve the effect according to the invention. These are, as a rule, anionic groups which are attached either at the end of the molecule and/or as side group on the oligomeric or polymeric backbone of the anionic polyelectrolyte.

The term "anionic" or "anionic groups" means for the purpose of the present invention both functional groups which are converted into the anionic form only after addition of a basic compound, usually with elimination of a protein, and functional groups already in anionic form with a suitable counter ion.

Examples of suitable counter ions are metal cations. These are in particular cations of the alkali metals, such as lithium, sodium or potassium. Likewise suitable as counter ions are the quaternary ammonium ions obtainable, for example, from amino compounds by protonation with acids.

However, the anionic polyelectrolytes preferably employed for the purpose of the present invention are those whose anionic groups are in the acidic, ie. nonneutralized, form.

It is preferred for the purpose of the present invention to employ anionic polyelectrolytes which are at least dispersible in aqueous solution, preferably in water itself, because crystallization from aqueous solution is preferred for the purpose of the present invention. However, the anionic polyelectrolyte is preferably soluble in water, where solubility in water means the formation of molecular solutions of the anionic polyelectrolytes. Since the solubility in water of the anionic polyelectrolyte is at least substantially determined by its anionic groups, the anionic polyelectrolytes which are preferably to be used are those having a number of anionic groups which is sufficient to produce solubility in water.

However, it is equally conceivable to use anionic polyelectrolytes whose number of anionic groups is insufficient to produce solubility in water. However, anionic polyelectrolytes of this type then have other hydrophilic units in the molecule to produce solubility in water, for example polyether units.

For the purpose of the present invention, at least one anionic polyelectrolyte is added to the solution containing at least the dicarboxylic acid to be crystallized. However, it is also possible for the purpose of the invention to employ mixtures of two or more different anionic polyelectrolytes as crystallization aids.

In this case it is also possible to use mixtures of anionic polyelectrolytes with different molecular weights.

The polyelectrolyte is, as a rule, added in an amount of at least about 0.01 ppm based on the solution to be crystallized. A reasonable upper limit for the amount added is about 300 ppm. It is likewise possible to add larger amounts to achieve the effect according to the invention, but they do not as a rule result in an improvement in the crystals.

The solution employed in the process according to the invention thus contains, besides the dicarboxylic acid to be crystallized, at least one anionic polyelectrolyte, as a rule in an amount of about 0.001 to about 300 ppm, but preferably in an amount of about 0.05 to about 200 ppm or about 0.1 to about 150 ppm. The polyelectrolyte is particularly preferably employed in an amount of about 1 to about 80 ppm. The stated amounts are based in each case on the entire solution to be crystallized.

In view of the small amount, which is to be added for the purpose of the present invention, of anionic polyelectrolyte and the large excess of dicarboxylic acid to be crystallized, it is also possible to employ an anionic polyelectrolyte with neutralized anionic groups, accepting very slight contamination with traces of the base used to neutralize the anionic polyelectrolyte. However, the use of neutralized anionic polyelectrolytes is not preferred.

The anionic polyelectrolyte may have as functional group, for example, carboxyl groups, sulfo groups or phosphono groups or mixtures of two or more thereof. However, the anionic polyelectrolyte preferably has carboxyl or sulfo groups, with carboxyl groups being preferred for the purpose of the invention.

Suitable as at least one anionic polyelectrolyte is, for example, a polymer prepared from acrylic acid, methacrylic acid, maleic acid, fumaric acid, itaconic acid or mesaconic acid monomers, or a copolymer prepared from two or more of these monomers, or a copolymer prepared from at least one of these monomers and at least one other monomer which is free of carboxyl groups, or a mixture of two or more of these polymers or copolymers.

Examples of suitable monomers free of carboxyl groups are vinyl acetate, acrylamide, isobutene or other olefins amenable to polymerization. The polyelectrolyte usually contains the monomers free of carboxyl groups in an amount of up to about 40% by weight, preferably in an amount of only up to about 30% by weight. However, a smaller amount may also be advantageous, such as about 20% by weight, 15% by weight, 10% by weight or even less, for example only about 5% by weight or less.

It is advantageous for carrying out the process according to the invention if the anionic polyelectrolyte is itself likewise soluble in the solvent used to dissolve the dicarboxylic acid. However, because of the small amount to be added, it is unnecessary for the solubility to correspond to or even exceed that of the dicarboxylic acid. It is also possible to add anionic polyelectrolytes with a lower solubility.

In a preferred embodiment of the invention, polyacrylic acid having a molecular weight of about 250,000 is employed as anionic polyelectrolyte.

The dicarboxylic acid is crystallized in the process according to the invention from a solvent or a mixture of solvents. For the purpose of the invention, mixtures of solvents are also referred to as "solvents" unless expressly indicated otherwise.

Suitable in principle for the process according to the invention are all solvents in which the dicarboxylic acid to be crystallized and the crystallization aid have adequate solubility. It is usually advantageous to choose a solvent in which the dicarboxylic acid is very soluble at elevated temperature but whose solubility decreases, preferably decreases greatly, on reducing the temperature. It is possible to employ for this purpose both organic solvents and water or mixtures of water and one or more organic solvents. However, when aqueous solvents are used, as a rule formation of several solvent phases in the solvent mixture should be avoided.

Thus, if a mixture of water and an organic solvent or a mixture of water and a mixture of several organic solvents is employed in the process according to the invention, the organic solvent or the mixture of several organic solvents should have at least limited solubility in water, and be added to the water in an amount with which no phase separation occurs. Examples of suitable water-miscible organic solvents are ketones such as acetone or methyl ethyl ketone, or alcohols such as methanol or ethanol.

However, it is preferred for the purpose of the invention to employ water as solvent.

Crystallization normally takes place when a supersaturated solution of the dicarboxylic acid is present. There are various possibilities for initiating crystallization. One possibility is to produce supersaturation of the solution by reducing the amount of solvent, for example by continuously evaporating off the solvent under atmospheric or reduced pressure.

Another possibility is to dissolve the dicarboxylic acid in the solvent at elevated temperature, and to produce supersaturation by cooling the solvent to a lower temperature, finally resulting in crystallization.

It is likewise possible to apply both methods simultaneously. This means cooling the solution to a temperature below that at which the dicarboxylic acid was dissolved, although the temperature is still high enough for the solvent to evaporate, with or without a reduction in pressure.

Although it is possible in principle for the crystallization to be carried out at any temperature, because it takes place mainly because of the difference in solubility in the solvent at different temperatures, or because of the decrease in the amount of solvent due to evaporation, it is advantageous for practical reasons to choose a temperature of about 0° C. to about 100° C.

The process according to the invention can be carried out with any solutions of the organic dicarboxylic acids in the solvents described above, preferably in water. These solutions are usually prepared by dissolving a dicarboxylic acid in the solvent at elevated temperature. The amount of dicarboxylic acid added in this case is norm-ally that necessary to form a saturated solution. How-ever, it is also possible if desired to use solutions below this saturation limit.

If, for example, adipic acid is employed as dicarboxylic acid, it is advisable to carry out the crystallization starting from an approximately 30 to 60% strength solution of adipic acid in water (about 70-95° C.).

Crystallization is initiated by cooling the solution or by evaporating off the solvent, with or without a reduction in pressure, or by a combination of the two methods.

Before or during the crystallization it is then possible to add a polyelectrolyte having a molecular weight of at least 2000. The polyelectrolyte is preferably added before the crystallization.

The crystallization is initiated and carried out in a continuous or batchwise process by evaporating the solvent, cooling the solvent or a combination of the two methods, normally until the suspension contains about 30 to 40% by weight of solids. The crystals obtained in this way can be removed in centrifuges and other separation devices, for example suction filters, and be dried by any suitable processes. They have the advantages referred to at the outset without further treatment.

The process according to the invention can be carried out in all apparatus which can be used for this purpose.

The invention furthermore relates to dicarboxylic acid crystals which can be prepared by subjecting a solution containing at least one organic dicarboxylic acid and at least one anionic polyelectrolyte having a molecular weight of at least 2000 to a crystallization.

The dicarboxylic acid crystals aaccording to the invention usually contain at least 99.5% by weight of organic dicarboxylic acid. If particularly pure dicarboxylic acids are required, the content of organic dicarboxylic acid is correspondingly higher. Thus, the dicarboxylic acid crystals according to the invention can contain the organic dicarboxylic acid in an amount of at least about 99.5, 99.9, 99.95 or even 99.99% by weight or more (based on dry matter).

Besides the organic dicarboxylic acid and the anionic polyelectrolyte, the dicarboxylic acid crystals according to the invention may also contain other substances, as a rule impurities, in small amounts. In this case, the content of dicarboxylic acid together with the content of anionic polyelectrolyte and any other constituents present amount to 100% of the crystals.

The crystals according to the invention preferably contain adipic acid as dicarboxylic acid. Other constituents which may be present in this case are, for example, the usual impurities produced in the preparation of adipic acid by oxidizing a cyclohexanone/cyclohexanol mixture, such as maleic acid, glutaric acid, succinic acid, caproic acid, nitric acid and solvent residues, such as water.

The other constituents or impurities are usually present in an amount of about 1000 ppm, preferably less than 200 ppm and particularly preferably less than about 10 ppm (based on the particular constituent or the particular impurity) in the crystals.

The invention likewise relates to the use of an anionic polyelectrolyte having a molecular weight of at least 2000 for preparing dicarboxylic acid crystals.

The following examples serve to illustrate the process according to the invention in detail.

EXAMPLES

Example 1

A 35% by weight solution of adipic acid in water at 80° C. is introduced into a continuously operated 1l laboratory crystallizer, and 15 ppm of a polyacrylic acid (based on the complete solution) of molecular weight 250,000 are added. After the pressure has been reduced to 200 mbar, formation of solid is initiated by evaporating off water and cooling to 60° C. The solution is crystallized continuously, adding fresh feed of the same composition and periodically drawing off small amounts of suspension, for 8 hours until a stationary state is set up. At the end of the experiment, the suspension present in the crystallizer is removed by centrifugation in a screen bowl centrifuge at 600 g for three minutes. About 200 g of crystals with a residual moisture content of 3.2% and an average crystal size of 571 $\mu$m are obtained. After drying under waterpump vacuum at 60° C. for half an hour, the crystallites are stored in a closed vessel. The crystals, which consist of isometric particles, are free-flowing after four weeks.

The crystals obtainable according to the example differ from known adipic acid crystalline forms by being distinctly more compact while having a larger average diameter, and thus they have a smaller surface area than crystals obtainable by conventional processes and having a comparable average diameter, and have essentially hydrophobic surfaces as outward-directed surfaces.

Comparative Example

The same experiment without crystallization aid afforded crystals in the form of thin plates with an average crystal size of only 432 $\mu$m and an initial residual moisture content of 4.7%. Caking is moderate after storage in a closed vessel for only 24 hours, and is extreme after some weeks.

We claim:

1. A process for preparing dicarboxylic acid crystals from a solution containing at least one dicarboxylic acid which consists essentially of adding, before or during the crystallization, at least one polyelectrolyte in an amount of from 0.01 to 200 ppm, wherein the at least one dicarboxylic acid consists essentially of oxalic acid, malonic acid, succinic acid, glutaric acid, adipic acid, pimelic acid, maleic acid or fumaric acid, and wherein the at least one polyelectrolyte has a molecular weight of from 2,000 to 2,000,000, which polyelectrolyte is not a surfactant, and consists essentially of polymers or copolymers of acrylic acid, methacrylic acid, maleic acid, fumaric acid, itaconid acid or mesaconic acid, with each other or with at least one other monomer which is free of carboxylic groups.

2. The process of claim 1, wherein the at least one anionic polyelectrolyte has a molecular weight of from 20,000 to 500,000.

3. The process of claim 1, wherein polyacrylic acid having a molecular weight of 250,000 is employed as the least one anionic polyelectrolyte.

4. The process of claim 1, characterized in that the least one anionic polyelectrolyte is employed in an amount of from 0.1 to 150 ppm.

5. The process of claim 1, wherein adipic acid is employed as dicarboxylic acid.

6. The process of claim 2 wherein the molecular weight of the at least one anionic polyelectrolyte is from 100,000 to 500,000.

7. The process of claim 6 wherein the molecular weight of the at least one anionic polyelectrolyte is from about 200,000 to 300,000.

8. The process of claim 1 wherein the anionic groups of the polyelectrolyte are in the acidic form.

\* \* \* \* \*